United States Patent [19]
Banks et al.

[11] Patent Number: 6,077,859
[45] Date of Patent: Jun. 20, 2000

[54] PYRAZOLES

[75] Inventors: Bernard Joseph Banks; Richard Andrew Bentley, both of Sandwich, United Kingdom

[73] Assignee: Pfizer Inc., New York, N.Y.

[21] Appl. No.: 09/311,320

[22] Filed: May 13, 1999

[30] Foreign Application Priority Data

May 22, 1998 [GB] United Kingdom .................... 9811050

[51] Int. Cl.$^7$ .................... A61K 31/4439; C07D 231/16; C07D 401/04

[52] U.S. Cl. .................... 514/341; 514/406; 514/407; 546/275.4; 548/371.4; 548/373.1; 548/374.1; 548/376.1; 548/377.1

[58] Field of Search .................... 546/275.4; 514/341, 514/406, 407; 548/371.4, 373.1, 374.1, 376.1, 377.1

[56] References Cited

U.S. PATENT DOCUMENTS 5,401,700  3/1995  Sohn et al. .................... 504/106
5,504,215  4/1996  Talley et al. .................... 548/377.1

*Primary Examiner*—Joseph McKane
*Assistant Examiner*—Sonya Wright
*Attorney, Agent, or Firm*—P. D. Richardson; P. H. Ginsburg

[57] ABSTRACT

Compounds of formula (IA) and (IB),

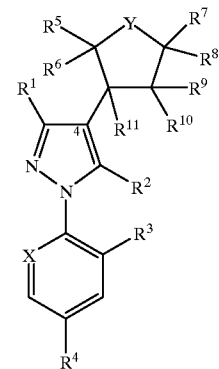

(IA)

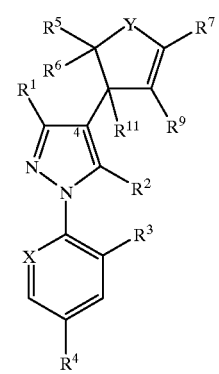

(IB)

wherein the substituents are as defined herein, and the salts and solvates thereof, are useful as antiparasitic agents.

21 Claims, No Drawings

PYRAZOLES

This invention relates to pyrazole derivatives, specifically 4-carbocyclyl-1-aryl pyrazoles, having parasiticidal properties,.

International Patent Application publication number WO98/24767 discloses certain antiparasitic 1-aryl-4-cyclopropylpyrazole substances.

International Patent Application Publication Number WO97/07102 discloses, inter alia, certain 1-aryl-4-(cyclohex-1-enyl)-pyrazole substances as antiparasitic agents.

According to the present invention, there are provided compounds of formula (IA) and (IB), (IA)

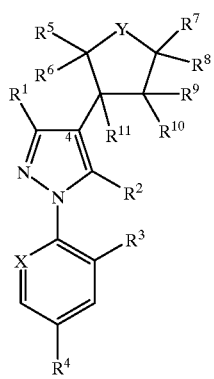

(IB)

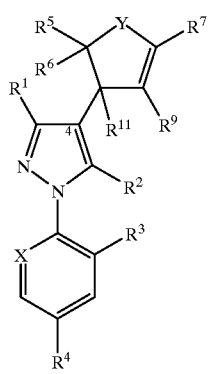

wherein $R^1$ is H, halo, $NH_2$, $CONH_2$, CN, $C_{1-6}$ alkyl optionally substituted by one or more substituents independently selected from halo and OH, $C_{2-6}$ alkanoyl optionally substituted by one or more halo, or $C_{2-6}$ alkenyl optionally substituted by one or more halo, $R^2$ is H, $C_{1-6}$ alkyl, $NH_2$ or halo, Y is an unbranched $C_{0-4}$ alkylene optionally bearing substituents independently selected from halo and $C_{1-6}$ alkyl, $R^5$, $R^6$, $R^7$, $R^8$, $R^9$ and $R^{10}$ are each independently H or halo, or $R^7$ and $R^8$ can be taken together to form an oxo or $=CR^{12}R^{13}$ moiety where $R^{12}$ and $R^{13}$ are each independently H or halo, $R^{11}$ is H, $C_{1-4}$ alkyl optionally substituted by one or more halo, or $C_{1-4}$ alkoxy optionally substituted by one or more halo, $R^3$ is halo, $R^4$ is $C_{1-4}$ alkyl optionally substituted by one or more halo, $C_{1-4}$ alkoxy optionally substituted by one or more halo, $S(O)_n(C_{1-4}$ alkyl optionally substituted by one or more halo), halo or $SF_5$, m is 0, 1, 2, 3 or 4, n is 0, 1 or 2, X is N or $CR^{14}$ where $R^{14}$ is halo, or a pharmaceutically-, agriculturally- or veterinarily-acceptable salt thereof, or solvate of any such compound or salt (hereinafter referred to as "the substances of the invention").

Alkyl and alkenyl groups may be straight or branched where the number of carbon atoms allows. $S(O)_n$alkyl, alkanoyl and alkoxy groups incorporate such alkyl moieties. "Halo" means fluoro, chloro, bromo or iodo.

Pharmaceutically-, agriculturally or veterinarily-acceptable salts are well-known in the art and include, for example those mentioned by Berge et al in J.Pharm.Sci., 66, 1–19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, gluconate, lactate, salicylate, citrate, tartrate, ascorbate, succinate, maleate, fumarate, fornate, benzoate, methanesulphonate, ethanesulphonate, benzenesulphonate and p-toluenesulphonate salts. Suitable base addition salts are formed from bases which form non-toxic salts and include the aluminium, calcium, lithium, magnesium, potassium, sodium, zinc and diethanolamine salts.

Solvates are generally well-known in the art.

Preferably $R^1$ is CN or $C_{1-6}$ alkyl optionally substituted by one or more halo.

More preferably $R^1$ is CN, $CH_3$ or $CF_3$.

Preferably $R^2$ is H, $NH_2$ or Cl.

More preferably $R^2$ is H or $NH_2$.

Preferably $R^3$ is Cl.

Preferably $R^4$ is $CF_3$, $OCF_3$ or $SF_5$.

Preferably Y is an unbranched $C_{0-4}$ alkylene.

Preferably X is N or C—Cl.

Preferably $R^5$ is H, Cl or F.

Preferably $R^6$ is H, Cl or F.

Preferably $R^7$ when taken on its own is H, Cl or F.

Preferably $R^8$ when taken on its own is H, Cl or F.

Preferably $R^7$ and $R^8$ when taken together are oxo, $CH_2$ or $CBr_2$.

Preferably $R^9$ is H.

Preferably $R^{10}$ is H.

Preferably $R^{11}$ is H, $CH_3$ or $CF_3$.

Preferably the 4-substituent on the pyrazole is a group selected from 2,2-dichloro-3-oxocyclobutyl, 2-chloro-2,3,3-trifluorocyclobutyl, 3-chloro-2,2,3-trifluorocyclobutyl, 3-oxocyclobutyl, 3,3-difluorocyclobutyl, 3-methylenylcyclobutyl, cyclobutyl, cyclopent-2-enyl, cyclohept-2-enyl, 3-dibromomethylenylcyclobutyl and cyclopentyl.

More preferably the 4-substituent on the pyrazole is a group selected from 2-chloro-2,3,3-trifluorocyclobutyl, 3-chloro-2,2,3-trifluorocyclobutyl, 3-oxocyclobutyl, 3,3-difluorocyclobutyl, 3-methylenylcyclobutyl, cyclobutyl, cyclopent-2-enyl, cyclohept-2-enyl and cyclopentyl.

The preferred specific substances are those of the Examples below, and the salts and solvates thereof.

The compounds of the formula (IA) and (IB) may possess one or more asymmetric centres and so exist in two or more stereoisomeric forms. The present invention includes all the individual stereoisomers of the compounds of formula (IA) and (IB), salts, solvates and mixtures thereof.

Separation of diastereomers may be achieved by conventional techniques, e.g. by fractional crystallisation, chromatography or H.P.L.C. of a stereoisomeric mixture of a compound of formula (IA) or (IB) or a suitable salt or derivative thereof. An individual enantiomer of a compound of formula (IA) or (IB) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base.

The compounds of the Examples and Preparations below can be prepared by a number of methods, such as the methods outlined below, and suitable adaptation thereof.

Unless otherwise specified, the substituents mentioned in the methods below are as defined above for the compounds of formulae (IA) and (IB)

Method 1(a)

Compounds of the formula (IA) where m is 0, $R^7$ and $R^8$ are taken together and are an oxo moiety, and $R^9$ and $R^{10}$ are chloro, i.e. compounds of formulae (IA(i)) below, can be made by reaction of a compound of formula (II) with a suitable reagent system such as zinc/trichloroacetyl chloride phosphorus oxychloride in a suitable solvent such as diethyl ether, such as is described in Example 6 below.

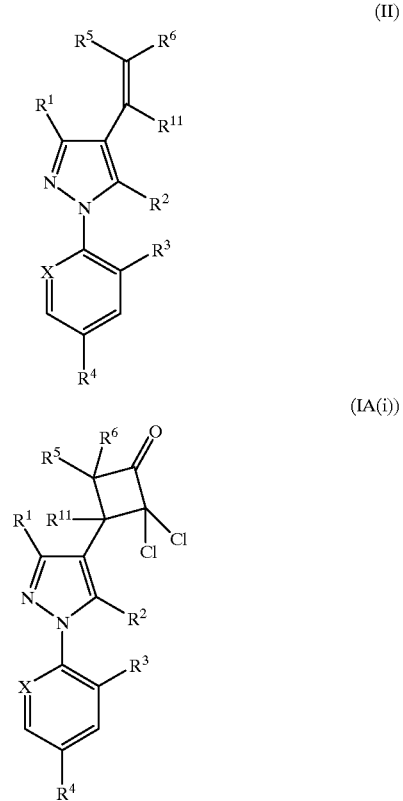

Compounds of formulae (II) above are available by the methods disclosed in International Patent Application Number WO97/07102 and suitable adaptation thereof.

Method 1(b)

α, α-dichloroketone compounds of formula (IA(i)), and homologues thereof of formula (IA) where m is 1,2,3 or 4, $R^7$ and $R^8$ are taken together as oxo, and $R^9$ and $R^{10}$ are chloro, can be transformed into the corresponding α, α-unsubstituted ketone by a suitable reduction with a number of systems, such as are described by J. March in "Advanced Organic Chemistry" (3rd or later editions), Wiley Interscience, in the reaction section 0–77 and references therein, herein incorporated by reference. An example of this reaction type is described below in Example 3.

Method 1(c)

Compounds of the formula (IA) wherein m is 0, $R^5$, $R^6$ and $R^{11}$ are all H, and $R^7$, $R^8$, $R^9$ and $R^{10}$ are all halo can be prepared by reaction of the compound of formula (II) above where $R^5$, $R^6$ and $R^{11}$ are all H, with an olefin of formula $R^7R^8C=CR^9R^{10}$ where $R^7$, $R^8$, $R^9$ and $R^{10}$ are all halo. A suitable method is to heat the reactants to elevated temperatures under increased pressure, such as in a steel "bomb". The method is exemplified below in Example 2.

Method 2

Compounds of formula (IA) wherein $R^7$ and $R^8$ are taken together as oxo (see Method 1 above) can be transformed into compounds of formula (IA) wherein $R^7$ and $R^8$ are taken together as $CR^{12}R^{13}$ via a suitable Wittig or similar reaction with a suitable phosphorus ylide reagent such as a phosphonium salt such as a "$CR^{12}R^{13}$-triphenylphosphonium bromide" with a suitable base in a suitable solvent. Such reactions are generally described in J.March in "Advanced Organic Chemistry" (3rd or later editions), Wiley Interscience, in the reaction section 6–47 and references therein, herein incorporated by reference. Examples of this reaction type are described below in Examples 5 and 12.

Method 3

Compounds of formula (IA) wherein $R^7$ and $R^8$ are taken together as oxo (see Method 1 above) can be transformed into gem-dihalide compounds of formula (IA) or (IB) wherein $R^7$ and $R^8$ are taken separately and are both halo by a suitable reaction of the type described in J. March in "Advanced Organic Chemistry" (3rd or later editions), Wiley Interscience, in the reaction section 6–25 and references therein, herein incorporated by reference. An example of this reaction type is described below in Example 4.

Method 4

Certain of the compounds of formulae (IA) and (IB) where $R^{11}$ is H can be made for instance by the transformation exemplified in Example 6.

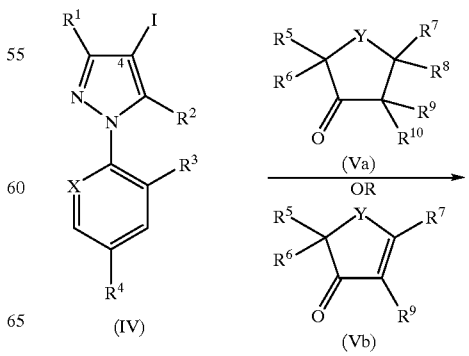

-continued

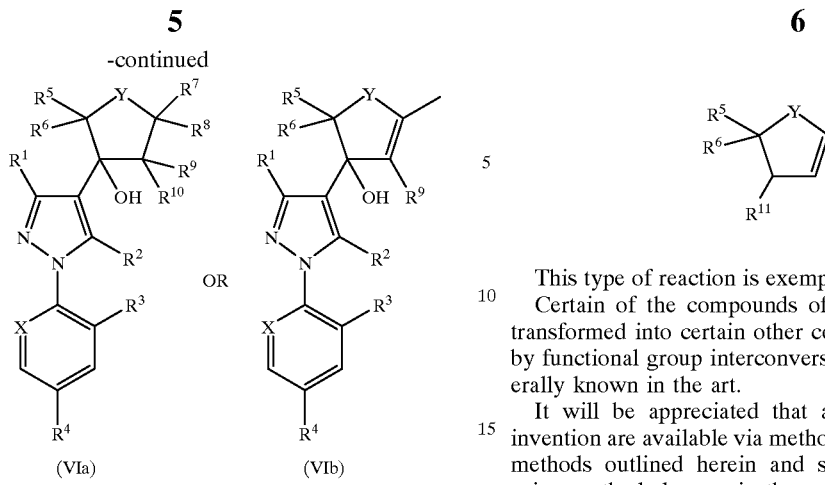

(VIa)    (VIb)

4-Iodopyrazoles of formulae (IV) are available by known methods and can be reacted with a suitable lithiating agent such as n-butyllithium in suitable conditions such as in tetrahydrofuran at reduced temperatures to give the corresponding 4-lithiated species. This can then be reacted with a ketone of formula (Va) or (Vb) to give the alcohol species (VIa) or (VIb) respectively as shown above.

Alcohols (VIa) and (VIb) can be reduced in a number of ways, for instance using the triethylsilane/boron trifluoride etherate system described in Example 6 below.

Ketones of formulae (Va) and (Vb) are available either commercially or via published methods.

Method 5(a)

Compounds of formula (IA) and (IB) where $R^2$ is H may be prepared from the corresponding compounds of formula (IA) or (IB) respectively where $R^2$ is $NH_2$, by reaction with an alkyl nitrite such as t-butyl nitrite, in N,N-dimethylformamide or tetrahydrofuran. This type of reaction is described in J. March in "Advanced Organic Chemistry" (3rd or later editions), Wiley Interscience, in the reaction section 4–23 and references therein, herein incorporated by reference. An example of this reaction type is described below in Example 8.

Method 5(b)

Compounds of formula (IA) and (IB) where $R^2$ is halo may be prepared from the corresponding compounds of formula (IA) or (IB) respectively where $R^2$ is $NH_2$, by reaction with an alkyl nitrite such as t-butyl nitrite, and a halide source. This type of reaction is described, inter alia, in J. March in "Advanced Organic Chemistry" (3rd or later editions), Wiley Interscience, in the reaction sections 3–24, 3–25, and 4–24 and references therein, herein incorporated by reference. An example of this reaction type is described below in Example 9.

Method 5(c)

Compounds of formula (IA) and (IB) where $R^2$ is $C_{1-6}$ alkyl may be prepared from the corresponding compounds of formula (IA) or (IB) respectively where $R^2$ is $NH_2$, by reaction with an alkyl nitrite such as t-butyl nitrite, and a reagent such as tetra($C_{1-6}$alkyl)tin. This type of reaction is described, inter alia, in J. March in "Advanced Organic Chemistry" (3rd or later editions), Wiley Interscience, in the reaction section 4–29, and references therein, herein incorporated by reference.

Method 6

Compounds of formula (IB) where $R^7$ and $R^9$ are H may be prepared from compounds of formula (IV) (see Method 4 above) via a palladium-catalysed cross-coupling reaction with a reagent of formula (VII):

(VII)

This type of reaction is exemplified below in Example 7.

Certain of the compounds of the invention may of be transformed into certain other compounds of the invention by functional group interconversions, etc. by methods generally known in the art.

It will be appreciated that all the compounds of the invention are available via methods known in the art and the methods outlined herein and suitable adaptation thereof using methods known in the art. The skilled chemist will exercise his skill and judgement as to any necessary adaptation, for instance in the choice of reagents, conditions, compatibility of starting materials and reagents with desired reaction, order of reaction, protection/deprotection, further reactions, etc.

It will be apparent to those skilled in the art that sensitive functional groups may need to be protected and deprotected during synthesis of substances of the invention. This may be achieved by conventional techniques, for example as described in "Protective Groups in Organic Synthesis" by T W Greene and P G M Wuts, John Wiley and Sons Inc, 1991.

The compounds of formula (I) and the salts and solvates thereof may be separated and purified by conventional methods.

The substances of the invention are useful because they possess parasiticidal activity in humans, animals and plants. They are particularly useful in the treatment of ectoparasites.

With regard to the use of the substances of the invention in humans, there is provided:

a) a pharmaceutical formulation comprising a substance of the invention in admixture with a pharmaceutically acceptable adjuvant, diluent or carrier which may be adapted for topical administration;

b) a substance of the invention, for use as a medicament;

c) the use of a substance of the invention in the manufacture of a parasiticidal medicament; and d) a method of treating a parasitic infestation in a patient which comprises administering an effective amount of a substance of the invention to the patient.

With regard to the use of the substances of the invention in non-human animals, the substances may be administered alone or in a formulation appropriate to the specific use envisaged and to the particular species of host animal being treated and the parasite involved. The methods by which the substances may be administered include oral administration by capsule, bolus, tablet or drench, or as a pour-on or spot-on formulation, or alternatively, they can be administered by injection (e.g. subcutaneously, intramuscularly or intravenously), dip, spray, mousse, shampoo, powder, or as an implant.

Such formulations are prepared in a conventional manner in accordance with standard veterinary practice. Thus capsules, boluses or tablets may be prepared by mixing the active compound/substance with a suitable finely divided diluent or carrier additionally containing a disintegrating agent and/or binder such as starch, lactose, talc, magnesium stearate etc. Oral drenches are prepared by dissolving or suspending the active ingredient in a suitable medium. Injectable formulations may be prepared in the form of a sterile solution which may contain other substances, for example, enough salts or glucose to make the solution isotonic with blood. Acceptable liquid carriers include the vegetable oils such as sesame oil and the like, glycerides such as triacetin and the like, esters such as benzyl benzoate, isopropyl myristate and fatty acid derivatives of propylene glycol and the like, as well as organic solvents such as pyrrolidone, glycerol formal and the like. The formulations are prepared by dissolving or suspending the active ingredient in the liquid carrier such that the final formulation contains from 0.01 to 10% by weight of the active ingredient.

These formulations will vary with regard to the weight of active substance contained therein depending on the species of host animal to be treated, the severity and type of infection and the body weight of the host. For parenteral, topical (e.g. using pour-on or spot-on, dip, spray, mousse, shampoo or powder to deliver the compound) and oral administration, typical dose ranges of the active ingredient are 0.01–100 mg per kg of body weight of the animal. Preferably the range is 0.1 to 10 mg per kg.

As an alternative the substances of the invention may be administered with the animal feedstuff and for this purpose a concentrated feed additive or premix may be prepared for mixing with the normal animal feed.

The substances of the invention have utility in the control of arthropod, plant nematode, helminth or protozoan pests. The substances of the invention may, in particular, be used in the field of veterinary medicine and livestock husbandry and in the maintenance of public health against arthropods, helminths or protozoa which are parasitic internally or externally upon vertebrates, particularly warm-blooded vertebrates, for example man and domestic animals, e.g. cattle, sheep, goats, equines, swine, poultry, dogs, cats and fish, for example Acarina, including ticks (e.g. Ixodes spp., Boophilus spp. e.g. *Boophilus microplus*, Amblyomma spp., Hyalomma spp., Rhipicephalus spp. e.g. *Rhipicephalus appendiculatus*, Haemaphysalis spp., Dermacentor spp., Ornithodorus spp. (e.g. *Ornithodorus moubata* and mites (e.g. Damalinia spp., *Dermahyssus gallinae*, Sarcoptes spp. e.g. *Sarcoptes scabiei*, Psoroptes spp., Chorioptes spp., Demodex spp., Eutrombicula spp.,) Diptera (e.g. Aedes spp., Anopheles spp., Musca spp., Hypoderma spp., Gastrophilus spp., Simulium spp.); Hemiptera (e.g. Triatoma spp.); Phthiraptera (e.g. Damalinia spp., Linoqnathus spp.) Siphonaptera (e.g. Ctenocephalides spp.); Dictyoptera (e.g. Periplaneta spp., Blatella spp.); Hymenoptera (e.g. *Monomorium pharaonis*); for example against infections of the gastrointestinal tract caused by parasitic nematode worms, for example members of the family Trichostrongylidae, *Nippostronylus brasiliensis, Trichinella spiralis, Haemonchus contortus, Trichostronylus colubriformis, Nematodirus battus, Ostertagia circumcincta, Trichostrongylus axei,* Cooperia spp. and *Hymenolepis nana,* in the control and treatment of protozoal diseases caused by, for example Eimeria spp. e.g. *Eimeria tenella, Eimeria acervulina, Eimeria brunetti, Eimeria maxima, Eimeria necatrix, Eimeria bovis, Eimeria zuerni* and *Eimeria ovinoidalis; Trypanosoma cruzi,* Leishmania spp., Plasmodium spp., Babesia spp., Trichomonadidae spp., Histomonas spp., Giardia spp., Toxoplasma spp., *Entamoeba histolytica* and Theileria spp.; in the protection of stored products, for example cereals, including grain and flour, groundnuts, animal foodstuffs, timber and household goods, e.g. carpets and textiles, against attack by arthropods, more especially beetles, including weevils, moths and mites, for example Ephestia spp. (flour moths), Anthrenus spp. (carpet beetles), Tribolium spp. (flour beetles), Sitophilus spp. (grain weevils) and Acarus spp. (mites), in the control of cockroaches, ants and terrnites and similar arthropod pests in infested domestic and industrial premises and in the control of mosquito larvae in waterways, wells, reservoirs or other running or standing water; for the treatment of foundations, structure and soil in the prevention of the attack on buildings by termites, for example, Reticulitermes spp., Heterotermes spp., Coptoterms spp.; in agriculture, against adults, larvae and eggs of Lepidoptera (butterflies and moths), e.g. Heliothis spp. such as *Heliothis virescens* (tobacco budworm), *Heliothis armioera* and *Heliothis zea*, Spodoptera spp. such as *S. exempta, S. littoralis* (Egyptian cotton worm), *S. eridania* (southern army worm), *Mamestra configurata* (bertha army worm); Earias spp. e.g. *E. insulana* (Egyptian bollworm), Pectinophora spp. e.g. *Pectinophora gossypiella* (pink bollworm), Ostrinia spp. such as *O.nubilalis* (European cornborer), *Trichoplusia ni* (cabbage looper), Pieris spp. (cabbage worms), Laphyqma spp. (army worms), Agrotis and Amathes spp. (cutworms), Wiseana spp. (porina moth), Chilo spp. (rice stem borer), Tryporyza spp. and Diatraea spp. (sugar cane borers and rice borers), *Sparganothis pilleriana* (grape berry moth), *Cydia pomonella* (codling moth), Archips spp. (fruit tree tortrix moths), *Plutella xylostella* (diamond black moth); against adult and larvae of Coleoptera (beetles) e.g. *Hypothenemus hampei* (coffee berry borer), Hylesinus spp. (bark beetles), *Anthonomus grandis* (cotton boll weevil), Acalymma spp. (cucumber beetles), Lema spp., Psylliodes spp)., *Leptinotarsa decemlineata* (Colorado potato beetle), Diabrotica spp. (corn rootworms), Gonocephalum spp. (false wire worms), Agriotes spp. (wireworms), Dermolepida and Heteronychus spp. (white grubs), *Phaedon cochleariae* (mustard beetle), *Lissorhoptrus oryzophilus* (rice water weevil), Melioethes spp. (pollen beetles), Ceutorhynchus spp., Rhynchophorus and Cosmopolites spp. (root weevils); against Hemiptera e.g. Psylla spp., Bemisia spp., Trialeurodes spp., Aphis spp., Myzus spp., *Megoura viciae*, Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp,., Pseucoccus spp., Helopeltis spp. (mosquito bugs), Lygus spp., Dysdercus spp., Oxycarenus spp., Nezara spp.; Nymenoptera e.g. Athalia spp. and Cephus spp. (saw flies), Atta spp. (leaf cutting ants); Diptera e.g. Hylemyia spp. (root flies), Atherigona spp. and Chlorops spp. (shoot flies), Phytomyza spp. (leaf miners), Ceratitis spp. (fruit flies); Thysanoptera such as *Thrips tabaci*: Orthoptera such as Locusta and Schistocerca spp. (locusts) and crickets e.g. Gryllus spp. and Acheta spp.; Collembola e.g. Sminthurus spp. and Onychiurus spp. (springtails), Isoptera e.g. Odontotermes spp. (termites), Dermaptera e.g. Forficula spp. (earwigs) and also other arthropods of agricultural significance such as Acari (mites) e.g. Tetranychus spp., Panonychus spp. and Bryobia spp. (spider mites), Eriophyes spp. (gall mites), Polyphacoutrsonemus spp.; Blaniulus spp. (millipedes), Scutigerella spp. (symphilids), Oniscus spp. (woodlice) and Triops spp. (crustacea); nematodes which attack plants and trees of importance to agriculture, forestry and horticulture either directly or by spreading bacterial, viral, mycoplasma or fungal diseases of the plants, root-knot nematodes such as Meliodogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*); lesion nematodes such as Pratylenchus spp. (e.g. *P. pratensis*); Belonoliamus spp. (e.g. *B. gracilis*); Tylenchulus spp. (e.g. *T semipenetrans*); Rotylenchulus spp. (e.g. *R. reniformis*); Rotylenchus spp. (e.g. *R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T. primitivus*); dagger nematodes such as Xiphinema spp. (e.g. *X. diversicaudatum*), Longidorus spp. (e.g. *L. elongatus*); Hoplolaimus spp. (e.g. *H. coronatus*); Aphelenchoides spp. (e.g. *A. ritzema-bosi, A. besseyi*); stem and bulb eelworms such as Ditylenchus spp. (e.g. *D. dipsaci*).

The substances of the invention also have utility in the control of arthropod or nematode pests of plants. The active substance is generally applied to the locus in which arthoropod or nematode infestation is to be controlled at a rate of about 0.005 kg to about 25 kg of active compound per hectare of locus treated, preferably 0.02 to 2 kg/ha. Under ideal conditions, depending on the pest to be controlled, the lower rate may offer adequate protection. On the other hand, adverse weather conditions, resistance of the pest and other factors may require that the active ingredient be used in higher proportions. For foliar application, a rate of 0.01 to 1 kg/ha may be used.

When the pest is soil-borne, the formulation containing the active substance is distributed evenly over the area to be treated in any convenient manner. Application may be made, if desired, to the field or crop-growing area generally or in close proximity to the seed or plant to be protected from attack. The active substance can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The substances of the invention may be applied in solid or liquid compositions to the soil principally to control those nematodes dwelling therein but also to the foliage principally to control those nematodes attacking the aerial parts of the plants (e.g. Aphelenchoides spp. and Ditylenchus spp. listed above).

The substances of the invention are of value in controlling pests which feed on parts of the plant remote from the point of application, e.g. leaf feeding insects are killed by the subject substances applied to roots. In addition the substances may reduce attacks on the plant by means of antifeeding or repellent effects.

The substances of the invention are of particular value in the protection of field, forage, plantation, glasshouse, orchard and vineyard crops, or ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobilds), or termites, for example, Reticulitermes spp., Heterotermes spp., Coptotermes spp.

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The substances of the invention are of value in the control of arthropods, helminths or protozoa which are injurious to, or spread or act as vectors of diseases in man and other animals, e.g. domestic animals, such as those hereinbefore mentioned, and more especially in the control of ticks, mites, lice, fleas, midges and biting, nuisance and myiasis flies. The substances of the invention are also useful in controlling arthropods, helminths or protozoa which are present, for example, inside domestic host animals or which feed in or on the skin or suck the blood of the animal, for which purpose they may be administered orally, parenterally, percutaneously or topically.

According to a further aspect of the invention, there is provided a parasiticidal formulation comprising a substance of the invention, in admixture with a compatible adjuvant, diluent or carrier. Preferably, the formulation is adapted for topical administration.

The invention further provides a substance of the invention for use as a parasiticide; and a method of treating a parasitic infestation at a locus, which comprises treatment of the locus with an effective amount of a substance of the invention. Preferably, the locus is the skin or fur of an animal, or a plant surface or the soil around the plant to be treated.

The invention further provides:

the processes described herein for preparing the compounds of formula (I) and salts and solvates thereof; pharmaceutical, veterinary or agricultural parasiticidal formulations comprising a compound of formula (IA) or (IB), or a pharnaceutically-, agriculturally- or veterinarily-acceptable salt and/or solvate thereof, in admixture with a compatible adjuvant, diluent or carrier; a compound of formula (IA) or IB), and pharmaceutically- or veterinarily-acceptable salts and/or solvates, and formulations thereof, for use as a medicament;

a method of treating a parasitic infestation at a locus, which comprises treating the locus with an effective amount of a compound of formula (IA) or (IB), or a salt or solvate of either entity, or formulation thereof;

the use of a compound of formula (IA) or (IB), or pharmaceutically- or veterinarily-acceptable salt thereof, or formulation thereof, in the manufacture of a medicament for the treatment of a parasitic infestation;

a method of killing or harming a parasite at a locus; and any novel intermediates described herein.

It is to be appreciated that reference to treatment includes prophylaxis as well as the alleviation of established symptoms of a condition, such as a parasitic infection.

Test for Insecticidal Activity

Adult flies (*Stomoxys calcitrans*) are collected and anaesthetized using $CO_2$. 1 $\mu$l of an acetone solution containing the test compound is applied directly to the thorax of the fly. Flies are then placed carefully into a 50 ml tube covered with damp gauze to recover from the $CO_2$. Negative controls have 1 $\mu$l of acetone dispensed onto them. Mortality is assessed 24 hours after dosing. The table below illustrates the in vivo activity of a selection of the substances of the invention against such flies. Dosages required to produce 100% mortality are expressed in μg/fly.

| Example No. | Dosage |
|---|---|
| 4 | 0.05 |
| 5 | 0.01 |
| 9 | 0.05 |
| 13 | 0.01 |

Test for Acaricidal Activity

A dose of 10 μg/cm² is created by evenly pipetting 0.5 ml of a 1 mg/ml solution of the test compound in a suitable solvent such as acetone or ethanol onto a Whatrnan No. 1 (Trade Mark) filter paper cut to a size of 8×6.25 cm. When dry, the paper is folded in half, sealed on two sides using a crimping device and placed in a Kilner jar containing a cotton wool pad dampened with water. The jar is then sealed and placed at 25° C. for 24 hours. Next, approximately 50 Boophilus microplus larvae are introduced into the treated paper envelope which is then crimped along the third side to effect a complete seal. The paper envelope is returned to the Kilner jar, which is sealed and placed at 25° C. for a further 48 hours. The papers are then removed and mortality assessed. Negative controls are provided by treating an appropriately cut filter paper with 0.5 ml of solvent only and following the same procedure. Activity at other doses is obtained by varying the concentration of the test solution. The table below illustrates the in vivo activity of a selection of the compounds of the invention against Boophilus microplus larvae. Dosages are expressed in μg/cm².

| Example No. | Dosage/%Mortality |
|---|---|
| 2 | 0.05/80% |
| 6 | 0.1/90% |

The invention is illustrated by the following Examples. In the Examples and Preparations, melting points were determined using a Gallenkamp melting point apparatus and are uncorrected. Nuclear magnetic resonance (NMR) data were obtained using a Bruker AC300 or AM300 and are quoted in parts per million using solvent or tetramethylsilane as reference.

Mass spectral (MS) data were obtained on a Finnigan Mat. TSQ 7000 or a Fisons Instruments Trio 1000. The calculated and observed ions quoted refer to the isotopic composition of lowest mass. HPLC purification was performed on a 21×250 mm Dynamaxr™ 5 μODS reverse-phase column eluted at 10 ml/minute with acetonitrile:water:methanol mixtures. Fractions were processed by evaporation of the non-aqueous components followed by partition between ether and saturated aqueous sodium hydrogen carbonate solution. The organic layer was then separated, dried and evaporated.

EXAMPLES

Example 1

3-Cyano-4-(2,2-dichloro-3-oxocyclobutyl)-1-(2,6-dichloro-4-trifluoromethylphenyl)pyrazole 3-Cyano-1-(2,2-dichloro-4-trifluoromethylphenyl)-4-vinylpyrazole (5.00 g, 15.06 mmol, WO97/07102-A1) was dissolved in anhydrous diethyl ether (50 ml) in a dry, nitrogen-flushed flask. Activated zinc (2.97 g, 45.8 mmol) was added and the suspension was vigorously stirred. A mixture of trichloroacetyl chloride (3.57 ml, 37.65 mmol) and phosphorus oxychloride (4.1 ml, 37.65 mmol) in diethyl ether (20 ml) was added dropwise at room temperature via a pressure-equalising dropping funnel over a period of 30 minutes—the resulting exotherm being controlled by the rate of addition. On completion of addition, the mixture was heated to reflux for 4 hr then cooled to room temperature. The mixture was filtered and poured onto 200 ml of crushed ice before extracting with diethyl ether (3×100 ml). The combined organics were washed successively with saturated aqueous $NaHCO_3$ solution and brine before drying over $MgSO_4$, filtering, and evaporating the ether in vacuo to leave a black oil. This was purified by silica chromatography (eluting with 10% diethyl ether/hexane) to give 3.80 g of the title compound as a white solid.

m.p.118.2–120.1° C.

$^1$H NMR $\delta$(CDCl$_3$): 3.70 (ddd, 2H), 4.35 (t, 1H), 7.70 (s, 1H), 7.80 (s, 2H).

MS (thermospray) M/Z 492.9; $C_{15}H_6Cl_4F_3N_3O$+$CH_3OH$+$NH_4$ requires 493.13.

Example 2

(I) 4-(2-Chloro-2,3,3-trifluorocyclobutyl)-3-cyano-1-(2,6-dichloro-4-trifluoromethylphenyl)pyrazole, and (II) 4-(3-chloro-2,3,3-trifluorocyclobutyl)-cyano-1-(2,6-dichloro-4-trifluoromethylphenyl) prazole 3-Cyano-1-(2,2-dichloro-4-trifluoromethylphenyl)-4-vinylpyrazole (500 mg, 1.51 mmol, WO97/07102-A1) was dissolved in methylene chloride (20 ml) in a steel bomb. The bomb was cooled in Cardice™ and an excess of chlorotrifluoroethylene was condensed into the bomb which was then sealed and heated to 130° C. for 48 hr. The reaction mixture was cooled to room temperature and the solvent removed in vacuo. The residue was purified by silica chromatography (eluting with 1:1 dichloromethane:hexane) followed by h.p.l.c. (Microsorb™ C18, eluting with acetonitrile/methanol/water 57:10:33 v/v) to give 120 mg of the title compounds as a mixture of isomers (1.4:1).

m.p.112.7–114.2° C.

$^1$H NMR $\delta$(CDCl$_3$): major isomer: 2.65–2.80 (m, 1H), 3.00–3.20 (m, 1H), 4.05–4.20 (m,1H), 7.65 (s, 1H), 7.75 (s, 2H); minor isomer: 2.85–2.95 (m, 1H), 3.25–3.45 (m, 1H), 3.95–4.05 (m, 1H), 7.70 (s, 1H), 7.75 (s, 2H).

MS (thermospray): M/Z 467.0; C15H6C13F6N3+NH4 requires 466.62.

Example 3

3-Cyano-4-(3-oxocyclobutyl)-1-(2,6-dichloro-4-trifluoromethylphenyl)pyrazole

3-Cyano-4-(2,2-dichloro-3-oxocyclobutyl)-1-(2,6-dichloro-4-trifluoromethylphenyl)pyrazole (3.00 g, 6.77 mmol, Example 1) was dissolved in dry toluene (60 ml) in a dry, nitrogen-flushed flask and cooled to 2° C. 2,2'-Azobisisobutyronitrile (134 mg, 0.81 mmol) was added in one portion followed by dropwise addition of tributyltin hydride (4.73 ml, 17.60 mmol) in dry toluene (10 ml). The mixture was allowed to slowly warm to room temperature and was stirred for 18 hr. The toluene was removed in vacuo and the residue dissolved in acetonitrile (50 ml). This solution was washed with hexane (4×50 ml) to remove organotin residues. The combined hexane fractions were extracted with acetonitrile (50 ml). The acetonitrile phases were combined and the solvent removed in vacuo to give a yellow oil. This was purified by silica chromatography (eluting with 10% diethyl ether/hexane) to yield 2.07 g of the title compound as a white solid.

m.p.127° C.

$^1$H NMR δ(CDCl$_3$): 2.25–2.40 (m, 2H), 2.65–2.80 (m, 3H), 7.55 (s, 1H), 7.80 (s, 2H).

MS (thermospray): M/Z 392.0; C15H8F3N3O+NH4 requires 392.19

Example 4

3-Cyano-1-(2,6-dichloro-4-trifluoromethylphenyl)-4-(3,3-difluorocyclobutyl)pyrazole 3-Cyano-4-(3-oxocyclobutyl)-1-(2,6-dichloro-4-trifluoromethylphenyl)pyrazole (200 mg, 0.53 mmol, Example 3) was dissolved in dry dichloromethane (DCM) (5 ml) in a dry, nitrogen-flushed flask and cooled to 0° C. Diethylaminosulfur trifluoride (0.14 ml, 0.53 mmol) was added dropwise. The reaction mixture gradually assumed a pale yellow colour and was allowed to warm to room temperature after stirring for 15 min at 0° C. After 4 hr, the mixture was diluted with DCM (50 ml) and washed successively with water (30 ml) and brine (30 ml). The organic phase was dried (MgSO$_4$), filtered and the solvent removed in vacuo. The residue was purified by silica chromatography (eluting with 33% DCM/hexane). The product was recrystallised from hexane to give 62 mg of the title compound as white plates.

m.p.127.9–129.0° C.

$^1$H NMR δ(CDCl$_3$): 2.60–2.80 (m, 2H), 3.05–3.30 (m, 2H), 3.55 (quin, 1H), 7.55 (s, 1H), 7.80 (s,2H).

MS (APCI): M/Z 396.2; C15H8C12F5N3 requires 396.15.

Example 5

3-Cyano-1-(2,6-dichloro-4-trifluoromethylphenyl)-4-(3-methylenecyclobutyl)pyrazole Methyltriphenylphosphonium bromide (304 mg, 0.85 mmol) was suspended in dry diethyl ether (5 ml) in a nitrogen-flushed flask and cooled to −5° C. n-Butyl lithium (0.34 ml, 2.5M in hexanes) was added dropwise producing a yellow colour. The mixture was warmed to room temperature before heating to reflux for 1 hr. The amber homogeneous solution thus obtained was cooled to −78° C. and 3-cyano-4-(3-oxocyclobutyl)-1-(2,6-dichloro-4-trifluoromethylphenyl)pyrazole (300 mg, 0.80 mmol, Example 3), dissolved in dry diethyl ether (5 ml), added dropwise keeping the internal temperature at ca. −70° C. The mixture was allowed to slowly warm to room temperature before refluxing for 1 hr. The mixture was then cooled, poured into water (20 ml) and extracted with diethyl ether (3×10 ml). The combined organics were washed with brine, dried (MgSO$_4$), filtered and ether solvent evaporated in vacuo. The residue was purified by silica chromatography (eluting with 20% DCM/hexane) yielding 40 mg of a white solid. This was further purified by hplc (Microsorb™C18, eluting with acetonitrile/methanol/water 6:1:3 v/v) to give 18 mg of the title compound.

m.p.10.3–111.7° C.

$^1$H NMR δ(CDCl$_3$): 2.80–2.95 (m, 2H), 3.20–3.35 (m, 2H), 3.65 (quin, 1H), 4.90 (dd, 2H), 7.50 (s, 1H), 7.75 (s, 2H).

MS (thermospray): M/Z 390.1; C16H10C12F3N3+NH4 requires 390.22.

Example 6

3-Cyano-4-cyclobutyl-1-(2,6-dichloro-4-trifluoromethethylphenyl)prazole

3-Cyano-4-(1-hydroxycyclobutyl)-1-(2,6-dichloro-4-trifluoromethylphenyl)pyrazole (180 mg, 0.48 mmol, Preparation 1) was dissolved in dry DCM (10 ml) in a dried, nitrogen-flushed flask and cooled to −78° C. Boron trifluoride diethyl etherate (0.24 ml, 1.92 mmol) was added dropwise, followed by triethylsilane (0.31 ml, 1.92 mmol) keeping the internal temperature at ca. −72° C. The reaction mixture was stirred with cooling for 1 hr, then allowed to slowly warm to room temperature and stirred a further 18 hrs. The reaction mixture was poured into water (20 ml) and extracted with DCM (2×20 ml). The combined organics were washed (brine), dried (Na$_2$SO$_4$), filtered and the solvent removed in vacuo to leave a yellow oil. This was purified by silica chromatography (eluting with 33% DCM/hexane) to yield the product as a white solid. This was recrystallised from hexane to give 80 mg of the title compound.

m.p.124.6–125.7° C.

$^1$H NMR δ(CDCl$_3$): 1.95 (m, 1H), 2.10 (q, 1H), 2.20 (m, 2H), 2.40–2.55 (m, 2H), 3.65 (m, 1H), 7.45 (s, 1H), 7.75 (s, 1H).

MS (thermospray) M/Z 378.3; C15H10 C12F3N3+NH4 requires 378.20.

Example 7

5-Amino-3-cyano-4-(cyclopent-2-enyl)-1-(2,6-dichloro-4-trifluoromethylphenyl)prazole To 5-amino-3-cyano-4-iodo-1-(2,6-dichloro-4-trifluoromethylphenyl)pyrazole (2.23 g, 5 mmol, WO97/07102) and cyclopentene (1 g, 15 mmol) in dry N,N-dimethylformamide (DMF) (25 ml), under a nitrogen atmosphere, was added bis(triphenylphosphine)palladium dichloride (175 mg, 0.25 mmol), cuprous iodide (100 mg) and triethylamine (2 ml). The mixture was heated to 70° C. for 4 hr. A further 1 g of cyclopentene was added and the mixture heated at 70° C. for 8 h. The cooled mixture was partitioned between DCM (75 ml) and water (75 ml), the organic phase was washed with water (2×75 ml) and dried (MgSO$_4$). After filtration the solvent was removed in vacuo to leave a brown oil. This was purified by silica chromatography (eluting with DCM). The resulting cream solid was recrystallised from cyclohexane to yield 564 mg of the title compound as a cream solid.

m.p.143–146° C.

$^1$H NMR δ(CDCl$_3$): 1.80 (m, 1H), 2.45–2.65 (m, 3H), 3.60 (br, 2H), 4.00 (m, 1H), 5,80 (m, 1H), 6.10 (m, 1H), 7.80 (s, 2H).

MS (thermospray): M/Z 387.2; C16H11C12F3N4+H requires 387.2.

Example 8

3-Cyano-4-(cyclopent-2-enyl)-1-(2,6-dichloro-4-trifluoromethylphenyl)pyrazole

To 5-amino-3-cyano-4-(cyclopent-2-enyl)-1-(2,6-dichloro-4-trifluoromethylphenyl)-pyrazole (300 mg, 0.77 mmol, Example 7) in dry tetrahydrofuran (THF) (8 ml)

heated at 65° C. was added dropwise tert-butyl nitrite (239 mg, 2.3 mmol) in dry THF (2 ml) over 30 min. The solution was heated for a further 3 hr at 65–70° C. The solvent was removed in vacuo and the resulting brown oil was purified by silica chromatography (eluting with DCM) to yield 170 mg of the title compound as a white solid.

m.p.76–80° C.

$^1$H NMR δ(CDCl$_3$): 1.80 (m, 1H), 2.40–2.60 (m, 3H), 4.05 (m, 1H), 5.80 (m, 1H), 6.00 (m, 1H), 7.39 (s, 1H), 7.80 (s, 2H).

MS (thermospray): M/Z 372.0; C16H10Cl12F3N3+H requires 372.18.

Example 9

5-Chloro-3-cyano-4-(cyclopent-2-enyl)-1-(2,6-dichloro-4-trifluoromethylphenyl)pyrazole To 5-amino-3-cyano-4-(cyclopent-2-enyl)-1-(2,6-dichloro-4-trifluoromethylphenyl)-pyrazole (500 mg, 1.3 mmol, Example 8) and cupric chloride (520 mg, 3.9 mmol) in dry acetonitrile (10 ml) at room temperature was added dropwise tert-butyl nitrite (239 mg, 2.3 mmol) in dry THF (5 ml) over 10 min. The solution was stirred for a further 2 hr. The solvent was removed in vacuo and the resulting solid triturated with diethyl ether (25 ml) followed by DCM (20 ml). The combined organic phases were evaporated to dryness and again triturated with diethyl ether. The mixture was filtered and the filtrate evaporated to dryness. The solid was partitioned between water (15 ml) and diethyl ether (25 ml). The organic phase was separated and washed with water (10 ml) followed by brine (10 ml). The organic phase was dried (MgSO$_4$), filtered and the solvent removed in vacuo to afford a brown solid. The material was purified by silica chromatography (eluting with 10% diethyl ether in hexane) to yield 200 mg of the title compound as a white solid. This was crystallised from isopropanoi.

m.p.118–121° C.

$^1$H NMR δ(CDCl$_3$): 1.85 (m, 1H), 2.40–2.60 (m, 2H), 2.65 (m, 1H), 4.05 (m, 1H), 5.75 (m, 1H), 6.10 (m, 1H), 7.80 (s, 2H).

MS (thermnospray): M/Z 423.0; C16H9C13F3N3+NH4 requires 423.01.

Example 10

5-Amino-3-cyano-4-(cyclohept-2-enyl)-1-(2,6-dichloro-4-trifluoromethylphenyl)pyrazole To 5-amino-3-cyano-4-iodo-1-(2,6-dichloro-4-trifluoromethylphenyl)pyrazole (2.23 g, 5 mmol, WO97/07102) and cycloheptene (3 ml) in dry DMF (25 ml), under a nitrogen atmosphere, was added bis(triphenylphosphine)palladium dichloride (100 mg, 0.13 mmol), cuprous iodide (100 mg) and triethylamine (2 ml). The mixture was heated at 65° C. for 18 h. A further 3 ml of cycloheptene was added and the mixture heated at 70° C. for 82 h. The cooled mixture was poured into water (500 ml) and extracted with DCM (2×100 ml). The organic phase was dried (MgSO$_4$), filtered and the solvent removed in vacuo to leave a brown oil. This was purified by silica chromatography (eluting with hexane/diethyl ether 1/1 v/v). The resulting cream solid was further purified by silica chromatography (eluting with hexane, hexane/diethyl ether 19/1, hexane/diethyl ether 9/1 and finally hexane/diethyl ether 3/1) to yield 564 mg of the title compound as a cream solid.

m.p.158–159° C.

$^1$H NMR δ(CDCl$_3$): 1.45 (m, 1H), 1.80–2.40 (m, 6H), 2.55–2.85 (m, 2H), 2.50 (br, 1.33H), 3.61 (br, 0.66H), 5.80–6.02 (m, 2H), 7.77 (s, 2H).

MS (thermospray): MIZ 415.0; C18H15C12F3N4+H requires 415.25

Example 11

3-Cyano-4-(cyclohept-2-enyl)-1-(2,6-dichloro-4-trifluoromethylphenyl)-pyrazole

To 5-amino-3-cyano-4-(cyclohept-2-enyl)-1-(2,6-dichloro-4-trifluoromethylphenyl)-pyrazole (208 mg, 0.5 mmol, Example 10) in dry THF (8 ml) heated at 65° C. was added dropwise tert-butyl nitrite (160 mg, 1.5 mmol) in dry THF (2 ml) over 30 min. The solution was heated for a further 2 hr at 65–70° C. The solvent was removed in vacuo and the resulting brown oil purified by silica chromatography (eluting with hexane, hexane/diethyl ether 19/1, hexane/diethyl ether 9/1, hexane/diethyl ether 4/1, hexaneldiethyl ether 1/1, finally diethyl ether). The resulting orange solid was recrystallised from hexane to yield 80 mg of the title compound as a cream solid.

m.p.106–107° C.

$^1$H NMR δ(CDCl$_3$): 1.55 (m, 1H), 1.70–2.00 (m, 3H), 2.15–2.30 (m, 3H), 2.40–2.60 (m, 1.5H), 3.00 (m, 0.75H), 3.80 (m, 0.25H), 5.82 (m, 1H), 5.90 (m, 1H), 7.44(2×s, 1H), 7.75 (s, 2H). MS (thermospray):

M/Z 4176.0; C16H13C12F3N4+NH4 requires 417.26.

Example 12

3-Cyano-4-(3-dibromomethylenecyclobutyl)-1-(2,6-dichloro-4-trifluoromethylphenyl)pyrazole Triphenylphosphine (560 mg, 2.14 mmol) was dissolved in 2 ml anhydrous DCM and cooled to −10° C. Carbon tetrabromide (355 mg, 1.07 mmol in 2 ml DCM) was added dropwise to the cooled solution, producing an amber colour. 3-Cyano-4-(3-oxocyclobutyl)-1-(2,6-dichloro-4-trifluoromethylphenyl)pyrazole (200 mg, 0.53 mmol, Example 3) in DCM (2 ml) was added dropwise whereupon the reaction mixture assumed a brown colour. The reaction mixture was warmed to room temperature. After 0.5 hr the mixture was poured into water (20 ml) and extracted with DCM (3×20 ml). The combined organics were washed (brine), dried (Na$_2$SO$_4$), filtered and the solvent removed in vacuo to leave a brown solid. This was purified by silica chromatography (eluting with 50% DCM/hexane) to yield 230 mg of the title compound as a white solid.

m.p.139.9–141.1° C.

$^1$H NMR δ(CDCl$_3$): 2.70–2.85 (m, 2H), 3.15–3.30 (m, 2H), 3.65 (quin, 1H), 7.50 (s, 1H), 7.75 (s, 2H).

MS (thermospray): M/Z 548.2; C16H8Br2C12F3N3+NH4 requires 548.01.

Example 13

5-Amino-3-cyano-4-cyclopentyl-1-(2,6-dichloro-4-trifluoromethylphenyl)pyrazole

5-Amino-3-cyano-4-(cyclopent-2-enyl)-1-(2,6-dichloro-4-trifluoromethylphenyl)pyrazole (200 mg, 0.5 mmol, Example 7) in ethanol (10 ml) was hydrogenated at room temperature and 345 kPa (50 p.s.i.) over 10% palladium on charcoal for 9 h. The catalyst was removed by filtration, washed with ethanol and the combined filtrates concentrated in vacuo to yield an oil.

The residue was purified by h.p.l.c. (Microsorb™ C 18, eluting with acetonitrile/methanol/water 5:1:4 v/v) to give 35 mg of the title compound as a white solid.

m.p.160° C.

$^1$H NMR δ(CDCl$_3$): 1.70–1.90 (m, 6H), 2.10 (m, 2H), 2.90 (m, 1H), 3.45 (br, 2H), 7.78 (s, 2H).

MS (thermospray): M/Z 389.3; C16H13C12F3N4+H requires 389.05.

PREPARATIONS

Preparation 1

3-Cyano-4-(1-hydroxycyclobutyl)-1-(2,6-dichloro-4-trifluoromethylphenyl)pyrazole 3-Cyano-1-(2,2-dichloro-4-trifluoromethylphenyl)-4-iodopyrazole (500 mg, 1.16 mmol, WO9707102) was dissolved in THF (10 ml) in a dry, nitrogen-flushed flask and cooled to −78° C. n-Butyllithium 0.46 ml, 2.5M in hexanes) was added dropwise over a period of 30 min, keeping the internal temperature at ca. −72° C. The reaction mixture was stirred at −78° C. for 20 min. then cyclobutanone (0.10 ml, 1.28 mmol), dissolved in THF (4 ml), was added dropwise and the mixture was stirred for 1 hr at −78° C. before warming to −20° C. After 2 hr, the mixture was warmed to room temperature and stirred overnight. The reaction mixture was poured into aqueous ammonium chloride (20 ml) and extracted with diethyl ether (2×20 ml). The combined organics were washed (brine), dried (Na$_2$SO$_4$), filtered and the solvents removed in vacuo to leave a yellow oil. This was purified by silica chromatography (eluting with a solvent gradient of DCM to 3% methanol/DCM) to yield 256 mg as a clear gum.

$^1$H NMR δ(CDCl$_3$): 1.75–1.95 (m, 1H), 2.0–2.15 (m, 1H), 2.40–2.55 (m, 2H), 2.60–2.75 (m, 2H), 7.65 (s, 1H), 7.75 (s, 2H).

MS (themospray) M/Z 394.1; C15H10C12F3N3O+NH4 requires 394.20.

Preparation 2

3-Cyano-4-(2,2-dichloro-3-hydroxycyclobutyl-1-(2,6-dichloro-4-trifluoromethylphenyl)pyrazole Cerium (III) chloride heptahydrate (665 mg, 2.0 mmol) was added to 3-cyano-4-(2,2-dichloro-3-oxocyclobutyl)-1-(2,6-dichloro-4-trifluoromethylphenyl)pyrazole (890 mg, 2.0 mmol, Example 1) dissolved in ethanol (15 ml) and DCM (10 ml) and the mixture cooled to −40° C. Sodium borohydride (531 mg, 14.0 mmol) was added in one portion. The reaction mixture was stirred with cooling for 2 hr before warming to room temperature and pouring onto crushed ice (75 ml). This was extracted with DCM (2×50 ml). The combined organics were washed (brine), dried (Na$_2$SO$_4$), filtered and the solvent removed in vacuo. The residue was purified by silica chromatography (eluting with 1% methanol/DCM) to yield 168 mg of the title compound as a gum.

$^1$H NMR δ(CDCl$_3$): 2.20 (q, 1H), 2.75 (d, 1H), 2.85–2.95 (m, 1H), 3.85 (dd, 1H), 4.60 (q, 1H), 7.65 (s, 1H), 7.80 (s, 2H).

Preparation 3

3-Cyano-4-(2,2-dichloro-3-toluenesulphonylcyclobutyl)-1-(2,6-dichloro-4-trifluoromethylphenyl)pyrazole 3-Cyano-4-(2,2-dichloro-3-hydroxycyclobutyl)-1-(2,6-dichloro-4-trifluoromethylphenyl)pyrazole (628 mg, 1.41 mmol, Preparation 2) was dissolved in anhydrous DCM and cooled to 0° C. Triethylamine (0.27 ml, 1.98 mmol) was added dropwise followed by p-toluenesulfonyl chloride (297 mg, 1.56 mmol). The cooling bath was removed and the reaction mixture was stirred 18 hr at room temperature. The reaction mixture was poured into an equal volume of water and extracted with DCM (2×30 ml). The combined organics were washed successively with saturated sodium bicarbonate, brine then dried (Na$_2$SO$_4$), filtered and the solvent removed in vacuo. The residue was purified by silica chromatography (eluting with 33% DCM/hexane) to yield 131 mg of the title compound as an off-white solid.

$^1$H NMR δ(CDCl$_3$): 2.45 (s, 3H), 2.85–2.95 (m, 1H), 3.85 (q, 1H), 5.20 (t, 1H), 7.40 (d, 2H), 7.60, (s, 1H), 7.80 (s, 2H), 7.90 (d, 2H).

What is claimed is:

1. A compound of formula (IA) or (IB),

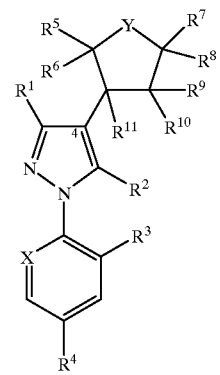

(IA)

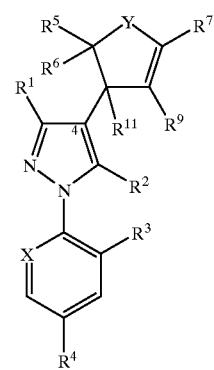

(IB)

wherein $R^1$ is H, halo, NH$_2$, CONH$_2$, CN, C$_{1-6}$ alkyl optionally substituted by one or more substituents independently selected from halo and OH, C$_{2-6}$ alkanoyl optionally substituted by one or more halo, or C$_{2-6}$ alkenyl optionally substituted by one or more halo, $R^2$ is H, C$_{1-6}$ alkyl, NH$_2$ or halo, Y is an unbranched C$_{0-4}$ alkylene optionally bearing substituents independently selected from halo and C$_{1-6}$ alkyl, $R^5$, $R^6$, $R^7$, $R^8$, $R^9$ and $R^{10}$ are each independently H or halo, or $R^7$ and $R^8$ can be taken together to form an oxo or =CR$^{12}$R$^{13}$ moiety where R$^{12}$ and R$^{13}$ are each independently H or halo, $R^{11}$ is H, C$_{1-4}$ alkyl optionally substituted by one or more halo, or C$_{1-4}$ alkoxy optionally substituted by one or more halo, $R^3$ is halo, $R^4$ is $C_{1-4}$ alkyl optionally substituted by one or more halo, $C_{1-4}$ alkoxy optionally substituted by one or more halo, $S(O)_n(C_{1-4}$ alkyl optionally substituted by one or more halo), halo or $SF_5$, m is 0, 1, 2, 3 or 4, n is 0, 1 or 2, X is N or $CR^{14}$ where $R^{14}$ is halo, or a pharmaceutically-, agriculturally- or veterinarily-acceptable salt thereof.

2. A compound or salt, according to claim 1 wherein $R^1$ is CN, $CH_3$ or $CF_3$.

3. A compound or salt according to claim wherein $R^2$ is H, $NH_2$ or Cl.

4. A compound or salt according to claim 1 wherein $R^3$ is Cl.

5. A compound or salt according to claim 1 wherein $R^4$ is $CF_3$, $OCF_3$ or $SF_5$.

6. A compound or salt according to claim 1 wherein X is N or C—Cl.

7. A compound or salt according to claim 1 wherein $R^5$ is H, Cl or F.

8. A compound or salt according to claim 1 wherein $R^6$ is H, Cl or F.

9. A compound or salt according to claim 1 wherein $R^7$ when taken on its own is H, Cl or F.

10. A compound or salt according to claim 1 wherein $R^8$ when taken on its own is H, Cl or F.

11. A compound or salt according to any one of claims 1 to 9 wherein $R^7$ and $R^8$ when taken together are oxo, $CH_2$ or $CBr_2$.

12. A compound or salt according to claim 1 wherein $R^9$ is H.

13. A compound or salt according to claim 1 wherein $R^{10}$ is H.

14. A compound or salt according to claim 1 wherein $R^{11}$ is H, $CH_3$ or $CF_3$.

15. A compound or salt according to claim 1 wherein the 4-substituent on the pyrazole is a group selected from 2,2-dichloro-3-oxocyclobutyl, 2-chloro-2,3,3-trifluorocyclobutyl, 3-chloro-2,2,3-trifluorocyclobutyl, 3-oxocyclobutyl, 3,3-difluorocyclobutyl, 3-methylenylcyclobutyl, cyclobutyl, cyclopent-2-enyl, cyclohept-2-enyl, 3-dibromomethylenylcyclobutyl and cyclopentyl.

16. A compound or salt according to claim 15 wherein the 4-substituent on the pyrazole is a group selected from 2-chloro-2,3,3-trifluorocyclobutyl, 3-chloro-2,2,3-trifluorocyclobutyl, 3-oxocyclobutyl, 3,3-difluorocyclobutyl, 3-methylenylcyclobutyl, cyclobutyl, cyclopent-2-enyl, cyclohept-2-enyl and cyclopentyl.

17. A compound or salt, according to claim 1, selected from, the group consisting of:

3-cyano-4-(2,2-dichloro-3-oxocyclobutyl)-1-(2,6-dichloro-4-trifluoromethylphenyl)pyrazole;

4-(2-Chloro-2,3,3-trifluorocyclobutyl)-3-cyano-1-(2,6-dichloro-4-trifluoromethylphenyl)pyrazole;

4-(3-chloro-2,2,3-trifluorocyclobutyl)-3-cyano-1-(2,6-dichloro-4-trifluoromethylphenyl)pyrazole;

3-cyano-4-(3-oxocyclobutyl)-1-(2,6-dichloro-4-trifluoromethylphenyl)pyrazole;

3-cyano-1-(2,6-dichloro-4-trifluoromethylphenyl)-4-(3,3-difluorocyclobutyl)pyrazole;

3-cyano-1-(2,6-dichloro-4-trifluoromethylphenyl)-4-(3-methylenecyclobutyl)pyrazole;

3-cyano-4-cyclobutyl-1-(2,6-dichloro-4-trifluoromethylphenyl)pyrazole;

5-amino-3-cyano-4-(cyclopent-2-enyl)-1-(2,6-dichloro-4-trifluoromethylphenyl)pyrazole;

3-cyano-4-(cyclopent-2-enyl)-1-(2,6-dichloro-4-trifluoromethylphenyl)pyrazole;

5-chloro-3-cyano-4-(cyclopent-2-enyl)-1-(2,6-dichloro-4-trifluoromethylphenyl)pyrazole;

5-amino-3-cyano-4-(cyclohept-2-enyl)-1-(2,6-dichloro-4-trifluoromethylphenyl)pyrazole;

3-cyano-4-(cyclohept-2-enyl)-1-(2,6-dichloro-4-trifluoromethylphenyl)-pyrazole;

3-cyano-4-(3-dibromomethylenecyclobutyl)-1-(2,6-dichloro-4-trifluoromethylphenyl)pyrazole; and 5-amino-3-cyano-4-cyclopentyl-1-(2,6-dichloro-4-trifluoromethylphenyl)pyrazole;

and the salts thereof.

18. A pharmaceutical or veterinary formulation comprising a substance according to any preceding claim, in admixture with a pharmaceutically or veterinarily acceptable adjuvant, diluent or carrier.

19. A formulation according to claim 18 which is adapted for topical administration.

20. A method of treating a parasitic infestation at a locus, in an animal patient, which comprises administering an effective amount of a substance according to any one of claims 1 to 5 and 7 to 18 to the locus.

21. A method of killing or harming a parasite which comprises administering an effective amount of a substance according to any one of claims 1 to 5 and 7 to 18 to the locus of the parasite.

* * * * *